(12) United States Patent
Xu et al.

(10) Patent No.: US 7,413,905 B2
(45) Date of Patent: *Aug. 19, 2008

(54) REAGENTS AND METHODS FOR CLASSIFYING LEUKOCYTES

(75) Inventors: Wenjuan Xu, Shenzhen (CN); Lina Zhang, Shenzhen (CN); Bing Liu, Shenzhen (CN)

(73) Assignee: Shenzhen Mindray Biomedical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/517,031

(22) Filed: Sep. 7, 2006

(65) Prior Publication Data

US 2007/0275469 A1   Nov. 29, 2007

(30) Foreign Application Priority Data

May 23, 2006 (CN) .................. 2006 1 0021034

(51) Int. Cl.
*G01N 31/00* (2006.01)
*G01N 33/48* (2006.01)

(52) U.S. Cl. .............................. 436/10; 436/8; 436/17; 436/18; 436/63; 436/164; 436/166; 436/174; 436/175; 435/2; 252/408.1

(58) Field of Classification Search ............... 436/8, 436/10, 17, 18, 63, 164, 166, 174, 175; 435/2, 435/4, 29; 422/82.05, 82.09; 252/408.1
See application file for complete search history.

(56) References Cited

U.S. PATENT DOCUMENTS

| | | | | |
|---|---|---|---|---|
| 4,528,274 A | * | 7/1985 | Carter et al. | 436/10 |
| 5,116,539 A | * | 5/1992 | Hamaguchi et al. | 516/77 |
| 5,155,044 A | * | 10/1992 | Ledis et al. | 436/17 |
| 5,180,677 A | * | 1/1993 | Di Ianni et al. | 436/17 |
| 5,242,832 A | * | 9/1993 | Sakata | 436/17 |
| 5,250,437 A | * | 10/1993 | Toda et al. | 436/10 |
| 5,389,549 A | * | 2/1995 | Hamaguchi et al. | 436/10 |
| 5,496,734 A | * | 3/1996 | Sakata | 436/63 |
| 5,518,928 A | * | 5/1996 | Cremins et al. | 436/10 |
| 5,538,893 A | * | 7/1996 | Sakata et al. | 436/10 |
| 5,618,733 A | * | 4/1997 | Sakata et al. | 436/17 |
| 5,639,630 A | * | 6/1997 | Malin et al. | 435/28 |
| 5,677,183 A | * | 10/1997 | Takarada et al. | 436/10 |
| 5,731,206 A | | 3/1998 | Ledis et al. | 436/17 |
| 5,786,224 A | * | 7/1998 | Li et al. | 436/63 |
| 5,817,518 A | * | 10/1998 | Li et al. | 436/63 |
| 5,821,128 A | * | 10/1998 | Provost | 436/63 |
| 5,843,608 A | * | 12/1998 | Li et al. | 436/63 |
| 5,958,776 A | * | 9/1999 | Sakata et al. | 436/10 |
| 6,114,130 A | * | 9/2000 | Veriac et al. | 435/7.24 |
| 6,210,969 B1 | * | 4/2001 | Li et al. | 436/10 |
| 6,214,625 B1 | * | 4/2001 | Li et al. | 436/10 |
| 6,869,798 B2 | * | 3/2005 | Crews et al. | 436/10 |
| 7,026,110 B1 | * | 4/2006 | Veriac et al. | 435/2 |

FOREIGN PATENT DOCUMENTS

| | | |
|---|---|---|
| CN | 1126836 A | 7/1996 |
| EP | 0 695 936 A2 | 6/1995 |
| JP | 08043381 | 2/1996 |
| WO | WO 88/07187 | 3/1988 |

OTHER PUBLICATIONS

State Intellectual Property Office Searching Report dated Jun. 13, 2006 for Chinese Patent Application No. 200610021034.
U.S. Appl. No. 11/516,900, filed Nov. 22, 2007, Xu et al.
Office Action mailed on Mar. 7, 2008 for U.S. Appl. No. 11/519,900.
Office Action mailed on Oct. 12, 2007 for U.S. Appl. No. 11/516,900.
Office Action mailed on May 14, 2007 for U.S. Appl. No. 11/516,900.
Notice of Allowance dated May 23, 2008 for U.S. Appl. No. 11/516,900.

* cited by examiner

*Primary Examiner*—Maureen M Wallenhorst
(74) *Attorney, Agent, or Firm*—Stoel Rives LLP; Kory D. Christensen; Matthew S. Bethards (57) ABSTRACT

The present invention relates to a reagent for classifying leukocytes including (a) at least one surfactant capable of lysing erythrocytes and partly damaging the cell membrane of leukocytes, (b) at least one organic compound bearing an anionic group capable of binding to the cationic component present in the leukocytes to provide morphological differences between the leukocytes, and (c) a buffer for adjusting pH to 2~8. Also disclosed is a method for classifying leukocytes into four groups.

10 Claims, 4 Drawing Sheets

REAGENTS AND METHODS FOR CLASSIFYING LEUKOCYTES

RELATED APPLICATIONS

This application claims priority to Chinese Patent Application No. 200610021034.4, filed May 23, 2006.

BACKGROUND OF THE INVENTION

1. Field of the Invention

The present invention relates to reagents and methods for classifying cells, and in particular, to reagents and methods for classifying leukocytes into four groups.

2. Description of the Related Art

In clinical testing fields, it is common and important to classifying and counting leukocytes in the whole blood of patients for diagnosis of diseases.

Till now, a number of devices and methods for classifying and counting leukocytes have been reported.

CN 95115317.X discloses a method for classifying leukocytes into five groups with two kinds of reagents. Both the reagents contain nonionic surfactants and a buffer. In addition, the first reagent for classifying the blood sample into four groups consisting of three groups corresponding to lymphocytes, monocytes and eosinophils and one group corresponding to neutrophils and basophils comprises at least one ionic surfactant, at least one organic compound having an anionic group and a buffer for adjusting pH, while the second reagent comprises at least one ionic surfactant for classifying the basophils from leukocytes other than basophils. By combining the information obtained with both reagents, this method classifies leukocytes into five groups. The detection system is based on laser light scattering. It is also emphasized that the nonionic surfactant is required and leukocytes will be lysed as a side effect which should be prevented.

U.S. Pat. No. 5,618,733 discloses a reagent for classifying and counting leukocytes. Specifically, it discloses a reagent for classifying leucocytes at least into four subgroups, which comprises at least one ionic surfactant, at least one organic compound, a nonionic surfactant and a buffer for adjusting pH. According to this patent, the reagent may comprise a first liquid and a second liquid, wherein said first liquid comprises at least one organic compound and wherein said second liquid comprises at least one ionic surfactant. It is also emphasized therein that each of said first and second liquids comprises a nonionic surfactant and a buffer, and the nonionic surfactant is necessary for dissolving the insoluble substance.

U.S. Pat. No. 5,389,549 relates to a method for classifying leukocytes employing the RF method and the DC method and a reagent used therefor. The reagent comprises a first fluid for diluting blood and which contains a hyperosmotic agent, a second fluid contains an anionic surfactant or a nonionic surfactant.

U.S. Pat. No. 5,538,893 relates to a reagent for classifying and counting leukocytes having at least one nonionic surfactant, at least one cationic surfactant, and a buffer.

Chinese Patent Application No. 88101677 relates to a method and reagent system for isolation and identification of leukocyte subpopulation. Said reagent system comprises a lytic reagent and a quench. The measuring techniques can be a radio frequency (RF) method or a direct current (DC) method.

U.S. Pat. No. 5,155,044 discloses a lytic reagent system for selective chemical treatment of whole blood, which comprises an acidic aqueous solution consisting essentially of a diluent, a lytic reagent and optionally a separate quench. The lytic reagent consists of formic acid, acetic acid and their respective mixtures. The reagent system can contain saponin in addition to the lytic reagent. And the pH value is in the range of from about 6 to about 7.5.

U.S. Pat. No. 5,731,206 discloses a lytic reagent composition and a kit of a lytic reagent system for the rapid isolation, identification and/or analysis of at least five subpopulations of leukocytes from a whole blood sample. The kit of a lytic reagent system comprises a first composition which decreases the pH of the sample to a pH in the range of from about 2.6 to about 4.0 containing saponin and carboxylic or sulfonic acid derivatives, and a second composition comprising a quench which stabilizes the blood sample at a pH in the range of from about 6 to about 7.5.

In U.S. Pat. No. 5,817,518, it discloses a reagent and method for differential determination of leukocytes in blood using DC and RF measurements. The lytic reagent comprises a nonionic surfactant that protects the neutrophil subpopulation from lysis. The pH value of the lytic reagent is adjusted to a pH in the range of from about 1.4 to about 3.4.

U.S. Pat. No. 5,510,267 provides a lytic agent and method enabling 5-part leukocyte differential count, wherein the lytic agent consists essentially of an aromatic oxyethanol, an organic buffer, and a nonionic detergent. The testing system is based on a four-angle laser light diffraction.

Among the above-mentioned prior art reagents and methods for classifying leukocytes, nonionic surfactants are necessary to the reagent for classification of CN95115317.X, U.S. Pat. No. 5,618,733, U.S. Pat. No. 5,389,549 and U.S. Pat. No. 5,538,893. There are also some restrictions on the pH value. Taking CN95115317.X for example, it is required that the pH value should be in the range of 5-11. All of these restrictions prevent the above-mentioned techniques from wide application.

Furthermore, with regard to the techniques for classifying described in CN 88101677, the most suitable condition is at normal temperature. With the changing of the ambient temperature, it is difficult to maintain the temperature constant at 25° C. The measurements fluctuate with the temperature and thus hurt the measurement precision. Under the circumstances, thermostatic apparatus are required to eliminate the influence of temperature changing. In addition, to keep the temperature at 25° C., not only heating devices but also cooling devices are necessary, which significantly increase the equipment costs.

Thus, there continues to be a need for improvement in the art for reagents and methods for classifying leukocytes that do not have the above drawbacks.

SUMMARY OF THE INVENTION

Surprisingly enough, the present inventors have found that the above needs as well as additional objects such as convenient applicability can be achieved by the reagents and methods of the present invention.

In one embodiment of the present invention, it is provided a reagent for classifying leukocytes into four groups consisting of three groups corresponding to lymphocytes, monocytes and eosinophils and one group corresponding to neutrophils and basophils, the reagent comprises:

(a) at least one surfactant capable of lysing erythrocytes and partly damaging the cell membrane of leukocytes, the at least one surfactant is selected from the group consisting of a nonionic surfactant, a cationic surfactant, an anionic surfactant, an ampholytic surfactant and a combination thereof, with the proviso that the combination of a cationic surfactant and an anionic surfactant is excluded;

(b) at least one organic compound bearing an anionic group capable of binding with a cationic component present in the leukocytes to give morphological differences between the leukocytes;

(c) a buffer for adjusting pH into a range of 2~8;

and when the at least one surfactant is a combination of a cationic surfactant and a nonionic surfactant or a combination of an anionic surfactant and a nonionic surfactant, the pH of the buffer is in the range of 2~4.5.

In a preferred embodiment, the present invention provides a reagent for classifying leukocytes into four groups consisting of three groups corresponding to lymphocytes, monocytes and eosinophils and one group corresponding to neutrophils and basophils, the reagent comprises:

(a) at least one surfactant capable of lysing erythrocytes and partly damaging the cell membrane of leukocytes, the at least one surfactant is selected from the group consisting of:

one or more cationic surfactants;

one or more anionic surfactants;

one or more ampholytic surfactants;

one or more nonionic surfactants;

a combination of one or more cationic surfactants and one or more ampholytic surfactants;

a combination of one or more anionic surfactants and one or more ampholytic surfactants;

a combination of one or more cationic surfactants and one or more nonionic surfactants;

a combination of one or more anionic surfactants and one or more nonionic surfactants;

a combination of one or more ampholytic surfactants and one or more nonionic surfactants;

a combination of one or more cationic surfactants, one or more ampholytic surfactants, and one or more nonionic surfactants; and a combination of one or more anionic surfactants, one or more ampholytic surfactants, and one or more nonionic surfactants;

(b) at least one organic compound bearing an anionic group capable of binding with a cationic component present in the leukocytes to give morphological differences between the leukocytes;

(c) a buffer for adjusting pH into a range of 2~8;

and when the at least one surfactant is a combination of a cationic surfactant and a nonionic surfactant or a combination of an anionic surfactant and a nonionic surfactant, the pH of the buffer is in the range of 2~4.5.

Surprisingly enough, the present inventors have also found that even without any nonionic surfactants, the classification of leukocytes is also achievable with the reagent of the present invention. Accordingly, in a further preferred embodiment, the present invention provides a reagent for classifying leukocytes into four groups consisting of three groups corresponding to lymphocytes, monocytes and eosinophils and one group corresponding to neutrophils and basophils, the reagent comprises:

(a) at least one surfactant capable of lysing erythrocytes and partly damaging the cell membrane of leukocytes, the at least one surfactant is selected from the group consisting of:

one or more cationic surfactants;

one or more anionic surfactants;

one or more ampholytic surfactants;

a combination of one or more cationic surfactants and one or more ampholytic surfactants; and a combination of one or more anionic surfactants and one or more ampholytic surfactants;

(b) at least one organic compound bearing an anionic group capable of binding with a cationic component present in the leukocytes to give morphological differences between the leukocytes;

(c) a buffer for adjusting pH into a range of 2~8.

Preferably, the reagent of the present invention may further contain alcohol(s) as a solubilizer.

According to the present invention, the nonionic surfactant that may be used is represented by the following formula I:

$$R_1-R_2-(CH_2CH_2O)_n-H \quad\quad I$$

wherein $R_1$ is a $C_8$-$C_{23}$ alkyl or alkenyl group, $R_2$ is —O— or —COO—, and n is an integer of 8-30.

According to the present invention, the cationic surfactant that may be used is a quaternary ammonium salt represented by the following formula II:

$$\{R_3-\underset{\underset{R_5}{|}}{\overset{\overset{R_4}{|}}{N^+}}-R_6\}\ X^-\quad\quad II$$

wherein $R_3$ is a $C_6$-$C_{14}$ alkyl or alkenyl group, $R_4$ and $R_5$ each independently is a $C_1$-$C_4$ alkyl or alkenyl group, $R_6$ is a $C_1$-$C_4$ alkyl or alkenyl group or a benzyl group; and X is a halogen.

According to the present invention, the anionic surfactant that may be used is sodium laurylsulfonate or a anionic surfactant represented by the following formula III $$R_7-R_8-(CH_2CH_2O)_n-Y \quad\quad III$$

wherein $R_7$ is a $C_8$-$C_{22}$ alkyl, alkenyl or alkynyl, $R_8$ is —O— or —COO—, n is an integer of 8-30, and Y is —SO$_3$Na, —COONa, —OSO$_3$Na or —ONa.

According to the present invention, the ampholytic surfactant that may be used is represented by the following formula IV:

$$R_9-\underset{\underset{R_{11}}{|}}{\overset{\overset{R_{10}}{|}}{N^+}}-CH_2COO^- \quad\quad IV$$

wherein $R_9$ is a $C_6$-$C_{14}$ alkyl or alkenyl, $R_{10}$ and $R_{11}$ each independently is a $C_1$-$C_4$ alkyl or alkenyl.

According to the present invention, the organic compound bearing an anionic group that may be used is selected from acidic dyes.

Also disclosed is a method for classifying leukocytes comprising the steps of: adding the reagent according to the present invention to a whole blood sample to classify the leukocytes into four groups consisting of three groups corresponding to lymphocytes, monocytes and eosinophils and one group corresponding to neutrophils and basophils, and classifying and counting each group by measuring the cell size information and the information on the morphological features.

According to the method of the present invention, the temperature at which the classification is carried out is in a range of 10~40° C. A temperature of 35° C. is particularly preferred.

For measuring the cell size information, a laser light scattering method with a low angle scattered light of 2°~6° is used. For measuring the information on the morphological features, a laser light scattering method with a high angle scattered light of 8°~20° is used.

As the major ingredients, the at least one surfactant used in the reagents according to the present invention is selected from the group consisting of various cationic surfactants, ionic surfactants, nonionic surfactants and ampholytic surfactants and a combination thereof (with the proviso that a combination of a cationic surfactant and an ionic surfactant is excluded). With the at least one surfactant according to the present invention, the classification can be carried out, and the measurement precision is ensured.

The temperature at which the classification is carried out according to the present invention can be selected from a temperature in the range of 10~40° C. As long as the temperature is kept at a constant temperature in this range, the stability of the classification is ensured. In addition, the capability of being carried out at a temperature higher than the room temperature makes it possible to provide a constant temperature with only heating device. The omission of a cooling device results in a saving of the equipment costs.

DETAILED DESCRIPTION OF THE INVENTION

The present invention provides reagents and methods for classifying leukocytes into four groups consisting of three groups corresponding to lymphocytes, monocytes and eosinophils and one group corresponding to neutrophils and basophils, and classifying and counting each group using a laser light scattering method by measuring information on the cell size information with low angle scattered light and the information on the morphological features with high angle scattered light.

The major ingredients of the reagent according to the present invention include at least one surfactant capable of lysing erythrocytes and partly damaging the cell membrane of leukocytes, at least one organic compound bearing an anionic group capable of binding with a cationic component present in leukocytes to give morphological differences between leukocytes, and a buffer for adjusting pH into a range of 2~8.

According to the present invention, the at least one surfactants used in the reagents may be selected from the group consisting of various cationic surfactants, ionic surfactants, nonionic surfactants and ampholytic surfactants and a combination thereof (with the proviso that a combination of a cationic surfactant and an ionic surfactant is excluded due to undesirable precipitation).

More specifically, in a preferred embodiment of the present invention, it is provided a reagent for classifying leukocytes into four groups consisting of three groups corresponding to lymphocytes, monocytes and eosinophils and one group corresponding to neutrophils and basophils, the reagent comprises:

(a) at least one surfactant capable of lysing erythrocytes and partly damaging the cell membrane of leukocytes, the at least one surfactant is selected from the group consisting of:
  one or more cationic surfactants;
  one or more anionic surfactants;
  one or more ampholytic surfactants;
  one or more nonionic surfactants;
  a combination of one or more cationic surfactants and one or more ampholytic surfactants;
  a combination of one or more anionic surfactants and one or more ampholytic surfactants;
  a combination of one or more cationic surfactants and one or more nonionic surfactants;
  a combination of one or more anionic surfactants and one or more nonionic surfactants;
  a combination of one or more ampholytic surfactants and one or more nonionic surfactants;
  a combination of one or more cationic surfactants, one or more ampholytic surfactants, and one or more nonionic surfactants; and
  a combination of one or more anionic surfactants, one or more ampholytic surfactants, and one or more nonionic surfactants;

(b) at least one organic compound bearing an anionic group capable of binding with a cationic component present in the leukocytes to give morphological differences between the leukocytes;

(c) a buffer for adjusting pH into a range of 2~8;

and when the at least one surfactant is a combination of a cationic surfactant and a nonionic surfactant or a combination of an anionic surfactant and a nonionic surfactant, the pH of the buffer is in the range of 2~4.5.

In a further preferred embodiment of the present invention, it is provided a reagent for classifying leukocytes into four groups consisting of three groups corresponding to lymphocytes, monocytes and eosinophils and one group corresponding to neutrophils and basophils, the reagent comprises:

(a) at least one surfactant capable of lysing erythrocytes and partly damaging the cell membrane of leukocytes, the at least one surfactant is selected from the group consisting of:
  one or more cationic surfactants;
  one or more anionic surfactants;
  one or more ampholytic surfactants;

a combination of one or more cationic surfactants and one or more ampholytic surfactants; and a combination of one or more anionic surfactants and one or more ampholytic surfactants;

(b) at least one organic compound bearing an anionic group capable of binding with a cationic component present in leukocytes to give morphological differences between leukocytes;

(c) a buffer for adjusting pH into a range of 2~8.

According to the present invention, a pH value in the range of 2~8 will suffice the requirement for the classification well. For a reagent comprising a combination of a cationic surfactant or an anionic surfactant with a nonionic surfactants, however, the pH value should be adjusted into the range of 2~4.5. Typically, there is no particular limitation on the type of the buffers. Any buffer system commonly used in the art, such as formate, phthalate, acetate, phosphate, TRIS and the like, may be used according to the present invention. The amount of the buffers used typically ranges from 10~500 mM.

According to the present invention, the nonionic surfactant that may be used is represented by the following formula I:

$$R_1\text{---}R_2\text{---}(CH_2CH_2O)_n\text{---}H \qquad\qquad I$$

wherein $R_1$ is a $C_8$-$C_{23}$ alkyl or alkenyl group, $R_2$ is —O— or —COO—, and n is an integer of 8~30. Examples of the $C_8$-$C_{23}$ alkyl or alkenyl group as $R_1$ include but are not limited to octyl, decyl, lauryl, tetradecyl, cetyl, stearyl and the like, particularly preferred are linear alkyls such as lauryl, tetradecyl and cetyl.

If present, the amount of the nonionic surfactant in the reagent according to the present invention should be sufficient to lyse erythrocytes and to partly damage the cell membrane of leukocytes. Specifically, it is suitable to use about 0.1~1%, preferably 0.1~0.7%, and most preferably 0.2~0.5% of nonionic surfactant based on the volume of the reagent according to the present invention (w/v), though this amount can be suitably modified depending upon the specific type of surfactant used.

According to the present invention, the cationic surfactant that may be used is a quaternary ammonium salt represented by the following formula II:

wherein $R_3$ is a $C_6$-$C_{14}$ alkyl or alkenyl group, $R_4$ and $R_5$ each independently is a $C_1$-$C_4$ alkyl or alkenyl group, $R_6$ is a $C_1$-$C_4$ alkyl or alkenyl group or a benzyl group; and X is a halogen. Examples of the $C_6$-$C_{14}$ alkyl or alkenyl group as $R_3$ include but are not limited to hexyl, octyl, decyl, lauryl, tetradecyl and the like, particularly preferred are linear alkyls such as octyl, decyl, lauryl and the like. Examples of the $C_1$-$C_4$ alkyl or alkenyl group as $R_4$ or $R_5$ include but are not limited to methyl, ethyl, propyl, butyl, butenyl and the like, preferably methyl, ethyl and propyl.

According to the present invention, the anionic surfactant that may be used is sodium laurylsulfonate or a anionic surfactant represented by the following formula III $$R_7\text{---}R_8\text{---}(CH_2CH_2O)_n\text{---}Y \qquad\qquad III$$

wherein $R_7$ is a $C_8$-$C_{22}$ alkyl, alkenyl, or alkynyl, $R_8$ is —O— or —COO—, n is an integer of 8-30, and Y is —SO$_3$Na, —COONa, —OSO$_3$Na, or —ONa. Examples of the $C_8$-$C_{22}$ alkyl, alkenyl, or alkynyl as $R_7$ include but are not limited to octyl, decyl, lauryl, tetradecyl and the like, particularly preferred are linear alkyls such as decyl and lauryl.

According to the present invention, the ampholytic surfactant that may be used is represented by the following formula IV:

wherein $R_9$ is a $C_6$-$C_{14}$ alkyl or alkenyl, $R_{10}$ and $R_{11}$ each independently is a $C_1$-$C_4$ alkyl or alkenyl. Examples of the $C_6$-$C_{14}$ alkyl or alkenyl as $R_9$ include but are not limited to hexyl, octyl, decyl, lauryl, tetradecyl and the like, particularly preferred are linear alkyls such as octyl, decyl and lauryl. Examples of the $C_1$-$C_4$ alkyl or alkenyl as $R_{10}$ or $R_{11}$ include but are not limited to methyl, ethyl, propyl, butyl, butenyl and the like, preferably, methyl, ethyl or propyl.

If present, the amount of the ionic surfactant in the reagent according to the present invention should be sufficient to lyse erythrocytes and to partly damage the cell membrane of leukocytes. Specifically, it is usually suitable to use about 50~6000 mg/L, preferably 200~5000 mg/L, and most preferably 500~4000 ml/L ionic surfactants, though this amount can be suitably modified depending upon the particular type of surfactant used.

Some kinds of surfactants and the preferable amount thereof are provided in Table 1. Any one of these surfactants or combination thereof except a combination of a cationic surfactant and an anionic surfactant may be used according to the present invention.

TABLE 1

| Preferable amount of some surfactants | |
|---|---|
| Surfactants | Preferable amount (mg/L) |
| Polyoxyethylene(8) stearic acid ether(Myrj 45) | 1000~8000 |
| Polyoxyethylene(10) cetyl ether (Brij 56) | 1000~8000 |
| Polyoxyethylene(23) cetyl ether (Brij 35) | 1000~5000 |
| Octyltrimethylammonium chloride (OTAC, PTI) | 2000~4000 |
| Octyltrimethylammonium bromide (OTAB, PTI) | 1500~3500 |
| Decyltrimethylammonium chloride (DTAC, PTI) | 1500~3000 |
| Decyltrimethylammonium bromide (DTAB, PTI) | 1000~2500 |
| Lauryltrimethylammonium chloride (LTAC, PTI) | 1000~2000 |
| Lauryltrimethylammonium bromide (LTAB, PTI) | 1000~1500 |
| Laurylpyridium chloride (PTI) | 500~1500 |
| Myristyltrimethylammonium chloride (MTAC, PTI) | 500~1000 |
| Myristyltrimethylammonium bromide (MTAB, PTI) | 500~1000 |
| Sodium lauryl polyoxyethylene(10) sulfonate | 1000~2000 |
| Sodium laurylsulfonate (SDS) | 1000~3000 |
| Lauryl glycine | 500~5000 |

Any kind of surfactant can be used as long as the hemolytic activity thereof is capable of resulting in pores in the cell membrane of leukocytes through which an organic compound for binding with cationic ions can pass. In addition, it is preferably used in an amount far less than the amount used for lysing the cell membrane so as to expose the cell nuclei.

The hemolytic activity of the surfactant is in proportion to the chain length of their side chain ($R_1$ of the nonionic surfactants of formula I, $R_3$ of the cationic surfactants of formula II, $R_7$ of the anionic surfactants of formula III, and $R_9$ of the ampholytic surfactants of formula IV) and, the more the carbon atom, the higher hemolytic activity they have, and the lower concentration is required.

As the major ingredients, the reagent according to the present invention further contains an organic compound capable of binding with a cationic component present in the leukocytes to give morphological differences between the leukocytes. Such an organic compound bears a hydrophobic group (such as an aromatic group, a hydrocarbon group having at least six carbon atoms and a heterocyclic ring having more than 6 carbon atoms) and an anionic group (such as carboxyl, sulfonic acid group). These organic compounds are negatively charged in aqueous solution and capable of binding with leukocytes to change the morphological features of leukocytes. There is no particular limitation on the types of the organic compounds and almost all kinds of acidic dyes can be used, such as Acid Blue series, Direct Blue, Acid Green, Acid Yellow, Acid Orange, Methyl Red, Methyl Orange, Aniline Blue, Alzarin Yellow and the like. The amount used ranges from 50 mg/L to 1000 mg/L, preferably from 100 mg/L to 500 mg/L.

According to the present invention, the reagent may further contain alcohol(s) as a solubilizer. There is no particular limitation on the types of alcohols. The examples of the alcohols that may be used according to the present invention include but are not limited to methanol, ethanol, isopropanol, n-butanol, 2-phenoxyethanol and the like. The amount of these alcohols ranges from about 0.1% to about 10% by volume of the reagent according to the present invention.

Additionally, the reagent of the present invention may contain a amount of NaCl to adjust the osmotic pressure into an appropriate range.

The reagent of the present invention may be formulated into one reagent or a combination of two separate reagents. As two separate reagents, their pH value may be the same or different. When two reagents are used in combination, additional organic dyes which bear a hydrophobic group and an anionic group may be included to isolate the eosinophils from granulocytes other than eosinophils.

The method for classifying leukocytes according to the present invention comprises the steps of: measuring the cell size information and the information on the morphological features after the reagent according to the present invention has been added into a whole blood sample for a period of time, classifying the leukocytes into four groups consisting of three groups corresponding to lymphocytes, monocytes and eosinophils and one group corresponding to neutrophils and basophils, and simultaneously counting the four groups of cells with a detection system.

There is no particular limitation on the ratio between the reagent of the present invention and the blood sample. Typically, it is suitable that the ratio between the reagent of the present invention and the blood sample is in a range of from 1:10 to 1:100. The detection may be carried out after the reagent of the present invention has been mixed with the blood sample for 12~30 seconds.

The temperature at which the classification is carried out according to the present invention can be selected from a temperature in the range of 10~40° C. As long as the temperature is kept at a constant temperature in this range, the stability of the classification is ensured. In addition, the capability of being carried out at a temperature higher than the room temperature makes it possible to provide a constant temperature with only heating device. The omission of a cooling device results in a saving of the equipment costs.

According to the present invention, a laser detecting method is preferably used for the measurement of the cell size information and the information on the morphological features. The devices for carrying out such a detection are known in the art. For measuring the cell size information, low angle scattered light of 2°~6° is used. For measuring the information on the morphological features, high angle scattered light of 8°~20° is used. The devices may be the one described in CN 95115317.X, or any others known in the art. And the detection of the scattered lights may be performed with the commonly used photodiode sensors.

In view of the above description and the examples below, one of ordinary skill in the art will be able to practice the invention as claimed without undue experimentation. The foregoing will be better understood with reference to the following examples that detail certain embodiments of the reagents or the methods according to the present invention. All references made to these examples are for the purposes of illustration. The following examples should not be considered exhaustive, but merely illustrative of only a few of the many embodiments contemplated by the present invention.

Unless otherwise indicated, an Auto Hematology Analyzer BC-5500(5200) from Shenzhen Mindray Bio-Medical Electronics Co., Ltd., Shenzhen, China is used for the detection of the scattered lights in all the examples. The reagents used are summarized in the following table.

| Chemicals | Purchased from |
| --- | --- |
| 2-phenoxyethanol | Protein Technologies, Inc., Tucson, AZ |
| Acid blue | Protein Technologies, Inc., Tucson, AZ |
| Lauryl glycine | Protein Technologies, Inc., Tucson, AZ |
| Decyltrimethylammonium bromide | Protein Technologies, Inc., Tucson, AZ |
| phthalic acid | Sigma Aldrich, St. Louis, MO |
| Brij 35 | Sigma Aldrich, St. Louis, MO |
| SDS | Sigma Aldrich, St. Louis, MO |
| Trihydroxymethylaminomethane | Sigma Aldrich, St. Louis, MO |
| NaCl | Guangzhou Chemical Reagent Factory, Guangzhou, China |
| Methanol | Guangzhou Chemical Reagent Factory, Guangzhou, China |
| Sodium biphosphate | Guangzhou Chemical Reagent Factory, Guangzhou, China |
| Disodium phosphate | Guangzhou Chemical Reagent Factory, Guangzhou, China |
| HCl | Guangzhou Chemical Reagent Factory, Guangzhou, China |
| Acetic acid | Guangzhou Chemical Reagent Factory, Guangzhou, China |
| Formic acid | Guangzhou Chemical Reagent Factory, Guangzhou, China |

EXAMPLE 1

A reagent used for classifying leukocytes into four groups having the following formulation was prepared.

| | |
| --- | --- |
| phthalic acid | 1 g |
| NaCl | 0.2 g |
| 2-phenoxyethanol | 10 g |
| Brij 35 | 3.4 g |

| | |
|---|---|
| Acid Blue | 0.15 g |
| water | to 1 L |
| pH | 2.5 |

The pH value of the reagent according to the above formulation was adjusted to 2.5, and the osmotic pressure was adjusted to 100 mOsm.

Figure 1:
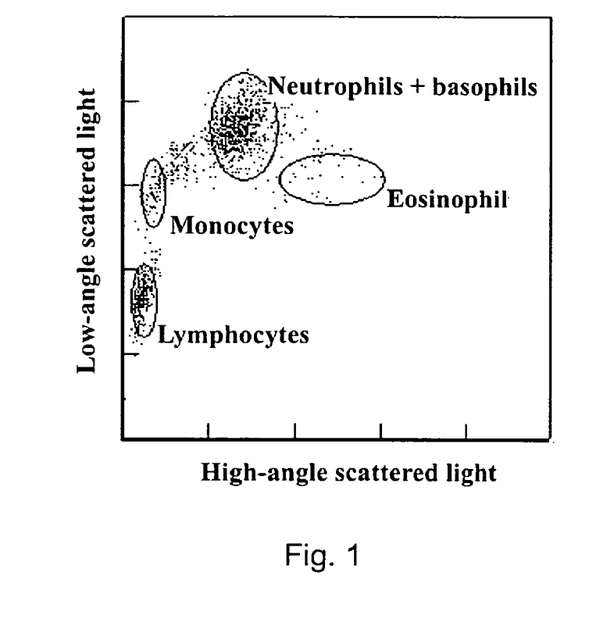
FIG. 1 is a scattergram showing the relationship between the intensity of the low angle scattered light and high angle scattered light when the reagent according to Example 1 is used for classifying leukocytes into four groups.

0.5 mL of the above reagent was added into 30 μl blood at a temperature maintained at 25° C. The leukocytes were tested by laser detecting method after being mixed for 12 seconds. Low angle scattered light of 2°~6° was used for measuring the cell size information and high angle scattered light of 8°~20° was used for measuring the information on morphological features. The result is shown in FIG. 1, in which the leukocytes are classified into four groups as lymphocyte group, monocyte group, eosinophil group, and neutrophil plus basophil group.

EXAMPLE 2

A reagent used for classifying leukocytes into four groups having the following formulation was prepared.

| | |
|---|---|
| NaCl | 0.2 g |
| Methanol | 2 g |
| SDS | 1.5 g |
| Sodium biphosphate | 3.08 g |
| Disodium phosphate | 4.87 g |
| Acid Blue | 0.15 g |
| water | to 1 L |
| pH | 6.5 |

The pH value of the reagent according to the above formulation was adjusted to 6.5, and the osmotic pressure was adjusted to 100 mOsm.

Figure 2:
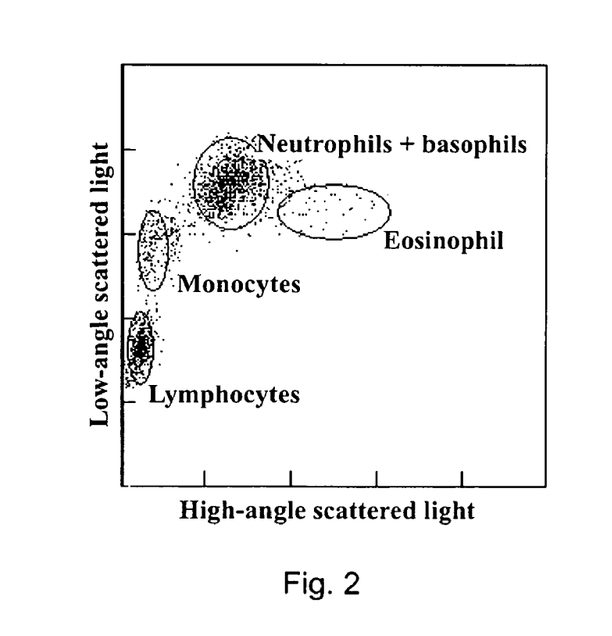
FIG. 2 is a scattergram showing the relationship between the intensity of the low angle scattered light and high angle scattered light when the reagent according to Example 2 is used for classifying leukocytes into four groups.

1 mL of the above reagent was added into 30 μl blood at a temperature maintained at 35° C. The leukocytes were tested by laser detecting method after being mixed for 20 seconds. Low angle scattered light of 2°~6° was used for measuring the cell size information and high angle scattered light of 8°~20° was used for measuring the information on morphological features. The result is shown in FIG. 2, in which the leukocytes are classified into four groups as lymphocyte group, monocyte group, eosinophil group, and neutrophil plus basophil group.

EXAMPLE 3

A reagent used for classifying leukocytes into four groups having the following formulation was prepared.

| | |
|---|---|
| NaCl | 0.3 g |
| Methanol | 3 g |
| Lauryl glycine | 1.2 g |
| Trihydroxymethylaminomethane | 3.05 g |
| HCl | 0.82 g |
| Acid Blue | 0.15 g |
| water | to 1 L |
| pH | 7.2 |

The pH value of the reagent according to the above formulation was adjusted to 7.2, and the osmotic pressure was adjusted to 140 mOsm.

Figure 3:
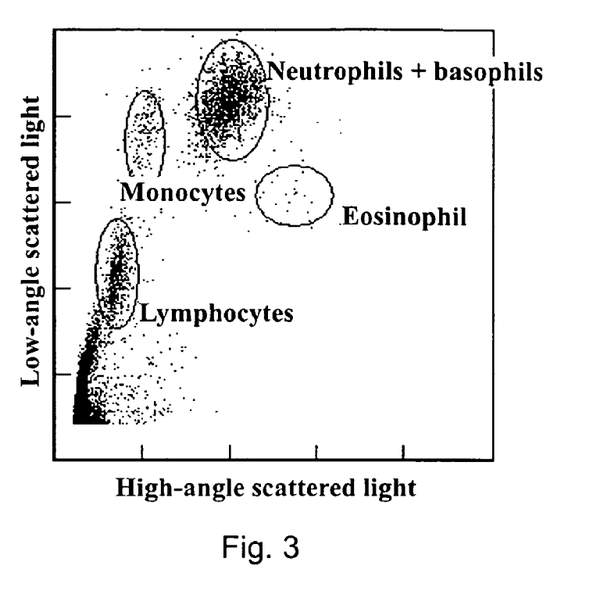
FIG. 3 is a scattergram showing the relationship between the intensity of the low angle scattered light and high angle scattered light when the reagent according to Example 3 is used for classifying leukocytes into four groups.

1.5 mL of the above reagent was added into 30 μl blood at a temperature maintained at 35° C. The leukocytes were tested by laser detecting method after being mixed for 20 seconds. Low angle scattered light of 2°~6° was used for measuring the cell size information and high angle scattered light of 8°~20° was used for measuring the information on morphological features. The result is shown in FIG. 3, in which the leukocytes are classified into four groups as lymphocyte group, monocyte group, eosinophil group, and neutrophil plus basophil group.

EXAMPLE 4

A reagent used for classifying leukocytes into four groups having the following formulation was prepared.

| | |
|---|---|
| NaCl | 0.3 g |
| 2-phenoxyethanol | 10 g |
| Decyltrimethylammonium bromide | 6.1 g |
| Acetic acid | 1.95 g |
| Acid Blue | 0.15 g |
| water | to 1 L |
| pH | 4.8 |

The pH value of the reagent according to the above formulation was adjusted to 4.8, and the osmotic pressure was adjusted to 140 mOsm.

Figure 4:
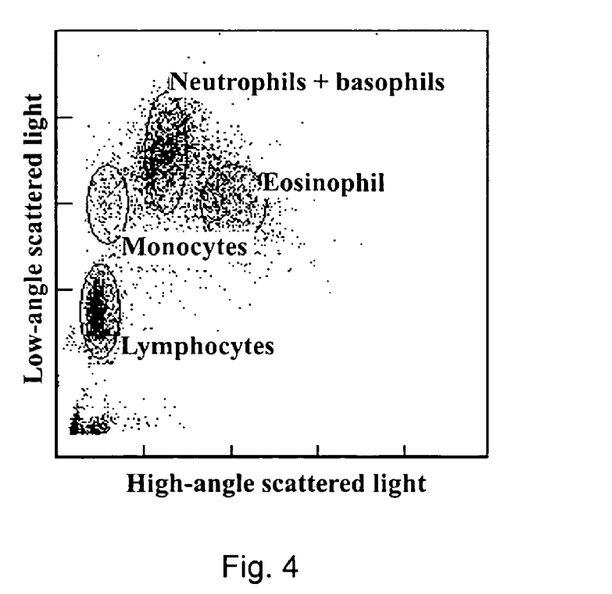
FIG. 4 is a scattergram showing the relationship between the intensity of the low angle scattered light and high angle scattered light when the reagent according to Example 4 is used for classifying leukocytes into four groups.

2 mL of the above reagent was added into 30 μl blood at a temperature maintained at 25° C. The leukocytes were tested by laser detecting method after being mixed for 30 seconds. Low angle scattered light of 2°~6° was used for measuring the cell size information and high angle scattered light of 8°~20° was used for measuring the information on morphological features. The result is shown in FIG. 4, in which the leukocytes are classified into four groups as lymphocyte group, monocyte group, eosinophil group, and neutrophil plus basophil group.

EXAMPLE 5

A reagent used for classifying leukocytes into four groups having the following formulation was prepared.

| | |
|---|---|
| NaCl | 0.2 g |
| Methanol | 2 g |
| Brij 35 | 1.4 g |
| SDS | 1.2 g |
| Formic acid | 1.3 g |
| Acid Blue | 0.15 g |
| water | to 1 L |
| pH | 3.8 |

The pH value of the reagent according to the above formulation was adjusted to 3.8, and the osmotic pressure was adjusted to 100 mOsm.

Figure 5:
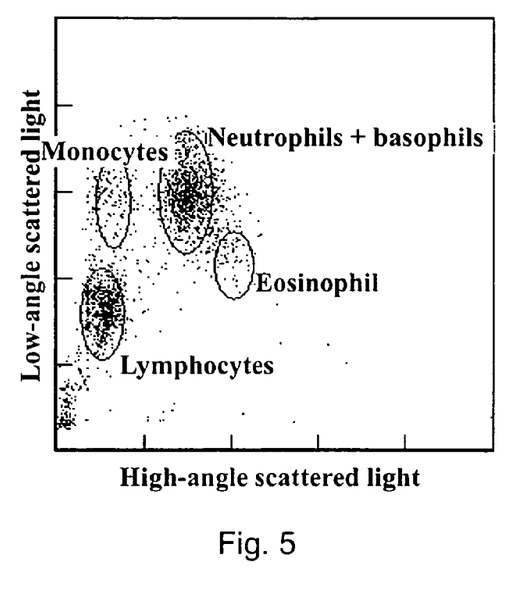
FIG. 5 is a scattergram showing the relationship between the intensity of the low angle scattered light and high angle scattered light when the reagent according to Example 5 is used for classifying leukocytes into four groups.

2 mL of the above reagent was added into 30 μl blood at a temperature maintained at 35° C. The leukocytes were tested by laser detecting method after being mixed for 15 seconds. Low angle scattered light of 2°~6° was used for measuring the cell size information and high angle scattered light of 8°~20° was used for measuring the information on morphological features. The result is shown in FIG. 5, in which the leukocytes are classified into four groups as lymphocyte group, monocyte group, eosinophil group, and neutrophil plus basophil group.

EXAMPLE 6

A reagent used for classifying leukocytes into four groups having the following formulation was prepared.

| | |
|---|---|
| NaCl | 0.2 g |
| Methanol | 2 g |
| Lauryl glycine | 1.2 g |
| SDS | 0.75 g |
| Sodium biphosphate | 3.08 |
| Disodium phosphate | 4.87 g |
| Acid Blue | 0.15 g |
| water | to 1 L |
| pH | 7.5 |

The pH value of the reagent according to the above formulation was adjusted to 7.5, and the osmotic pressure was adjusted to 100 mOsm.

Figure 6:
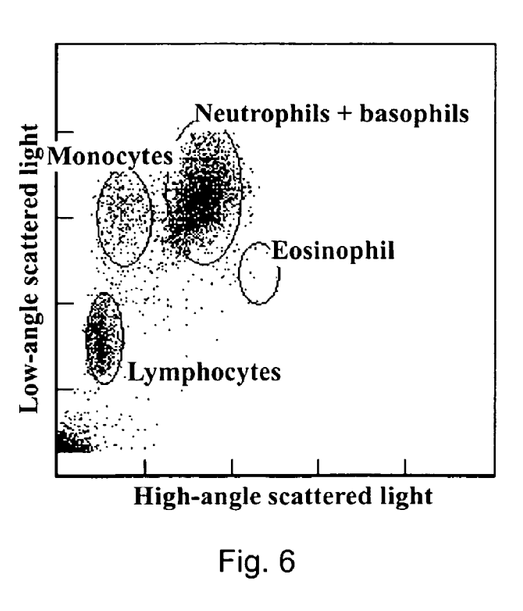
FIG. 6 is a scattergram showing the relationship between the intensity of the low angle scattered light and high angle scattered light when the reagent according to Example 6 is used for classifying leukocytes into four groups.

1 mL of the above reagent was added into 30 µl blood at a temperature maintained at 25° C. The leukocytes were tested by laser detecting method after being mixed for 15 seconds. Low angle scattered light of 2°~6° was used for measuring the cell size information and high angle scattered light of 8°~20° was used for measuring the information on morphological features. The result is shown in FIG. 6, in which the leukocytes are classified into four groups as lymphocyte group, monocyte group, eosinophil group, and neutrophil plus basophil group.

EXAMPLE 7

A reagent used for classifying leukocytes into four groups having the following formulation was prepared.

| | |
|---|---|
| phthalic acid | 1 g |
| NaCl | 0.2 g |
| 2-phenoxyethanol | 10 g |
| Decyltrimethylammonium bromide | 5.4 g |
| Lauryl glycine | 1.2 g |
| Acid Blue | 0.15 g |
| water | to 1 L |
| pH | 2.8 |

The pH value of the reagent according to the above formulation was adjusted to 2.8, and the osmotic pressure was adjusted to 130 mOsm.

Figure 7:
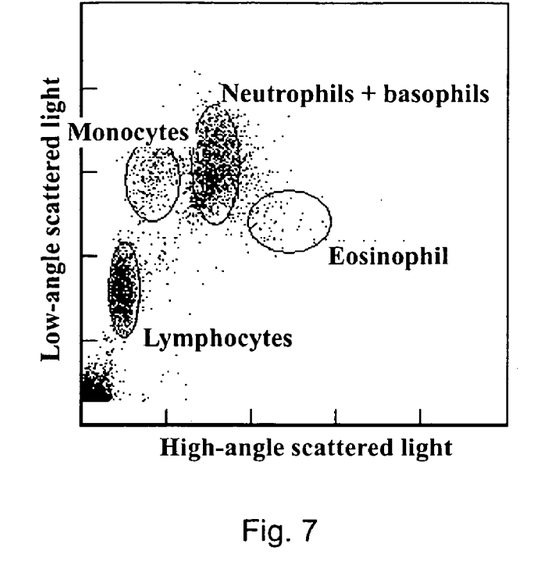
FIG. 7 is a scattergram showing the relationship between the intensity of the low angle scattered light and high angle scattered light when the reagent according to Example 7 is used for classifying leukocytes into four groups.

1.2 mL of the above reagent was added into 30 µl blood at a temperature maintained at 35° C. The leukocytes were tested by laser detecting method after being mixed for 14 seconds. Low angle scattered light of 2°~6° was used for measuring the cell size information and high angle scattered light of 8°~20° was used for measuring the information on morphological features. The result is shown in FIG. 7, in which the leukocytes are classified into four groups as lymphocyte group, monocyte group, eosinophil group, and neutrophil plus basophil group.

EXAMPLE 8

A reagent used for classifying leukocytes into four groups having the following formulation was prepared.

| | |
|---|---|
| phthalic acid | 1 g |
| NaCl | 0.2 g |
| 2-phenoxyethanol | 10 g |
| Brij 35 | 1.1 g |
| Decyltrimethylammonium bromide | 4.8 g |
| Lauryl glycine | 1.0 g |
| Acid Blue | 0.15 g |
| water | to 1 L |
| pH | 2.8 |

The pH value of the reagent according to the above formulation was adjusted to 2.8, and the osmotic pressure was adjusted to 126 mOsm.

Figure 8:
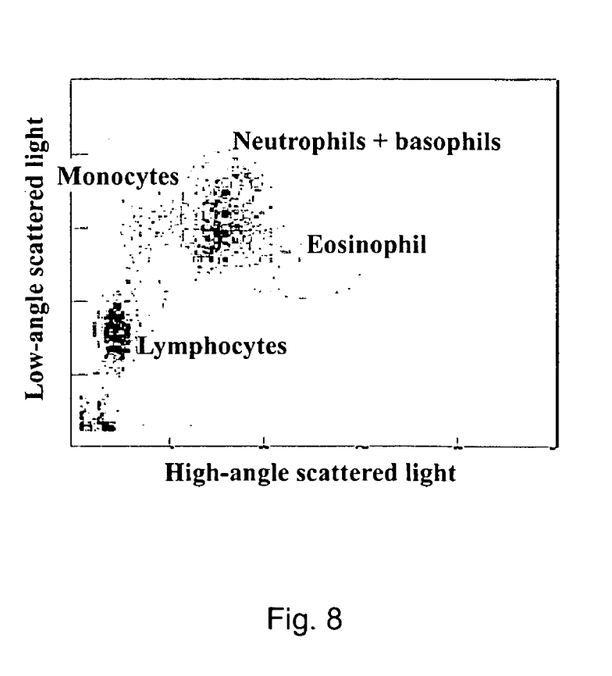
FIG. 8 is a scattergram showing the relationship between the intensity of the low angle scattered light and high angle scattered light when the reagent according to Example 8 is used for classifying leukocytes into four groups.

1.2 mL of the above reagent was added into 30 µl blood at a temperature maintained at 35° C. The leukocytes were tested by laser detecting method after being mixed for 14 seconds. Low angle scattered light of 2°~6° was used for measuring the cell size information and high angle scattered light of 8°~20° was used for measuring the information on morphological features. The result is shown in FIG. 8, in which the leukocytes are classified into four groups as lymphocyte group, monocyte group, eosinophil group, and neutrophil plus basophil group.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What we claim is:

1. A reagent for classifying leukocytes into four groups consisting of three groups corresponding to lymphocytes, monocytes and eosinophils and one group corresponding to neutrophils and basophils, the reagent comprises:

(a) at least one surfactant for lysing erythrocytes and partly damaging the cell membrane of leukocytes, the at least one surfactant is selected from the group consisting of:

one or more cationic surfactants;

one or more anionic surfactants;

one or more ampholytic surfactants;

a combination of one or more cationic surfactants and one or more ampholytic surfactants; and a combination of one or more anionic surfactants and one or more ampholytic surfactants;

(b) at least one organic compound bearing an anionic group for binding with a cationic component present in the leukocytes to give morphological differences between the leukocytes; and (c) a buffer for adjusting pH into a range of 2~8;

wherein the reagent is free from nonionic surfactants.

2. The reagent according to claim 1, further comprising an alcohol as a solubilizer.

3. The reagent according to claim 1, wherein the cationic surfactant is a quaternary ammonium salt represented by formula II:

II wherein $R_3$ is a $C_6$-$C_{14}$ alkyl or alkenyl group, $R_4$ and $R_5$ each independently is a $C_1$-$C_4$ alkyl or alkenyl group, $R_6$ is a $C_1$-$C_4$ alkyl or alkenyl group or a benzyl group; and X is a halogen.

4. The reagent according to claim 1, wherein the anionic surfactant is sodium laurylsulfonate or a anionic surfactant represented by formula III:

III wherein $R_7$ is a $C_8$-$C_{22}$ alkyl, alkenyl or alkynyl, $R_8$ is —O— or —COO—, n is an integer of 8-30, and Y is —$SO_3Na$, —COONa, —$OSO_3Na$ or —ONa.

5. The reagent according to claim 1, wherein the ampholytic surfactant is represented by formula IV:

IV wherein $R_9$ is a $C_6$-$C_{14}$ alkyl or alkenyl, $R_{10}$ and $R_{11}$ each independently is a $C_1$-$C_4$ alkyl or alkenyl.

6. The reagent according to claim 1, wherein the organic compound bearing an anionic group is an acidic dye.

7. A method for classifying leukocytes with the reagent according to any of claims 1~6, comprising the steps of: adding the regent to a whole blood sample to classify the leukocytes into four groups consisting of three groups corresponding to lymphocytes, monocytes and eosinophils and one group corresponding to neutrophils and basophils, and classifying and counting each group by measuring cell size information and information on morphological features.

8. The method according to claim 7, wherein the classification is carried out at a temperature in the range of 10~40° C.

9. The method according to claim 8, wherein the classification is carried out at 35° C.

10. The method according to claim 8, wherein a laser light scattering method with low angle scattered light of 2°~6° is used to measure the cell size information, and a laser light scattering method with high angle scattered light of 8°~20° is used to measure the information on morphological features.

* * * * *